(12) United States Patent
Shilov et al.

(10) Patent No.: US 8,712,695 B2
(45) Date of Patent: Apr. 29, 2014

(54) METHOD, SYSTEM, AND COMPUTER PROGRAM PRODUCT FOR SCORING THEORETICAL PEPTIDES

(75) Inventors: Ignat V. Shilov, San Jose, CA (US); Sean L. Seymour, Berkeley, CA (US); Ron Bonner, Newmarket (CA); Alpesh A. Patel, San Francisco, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 1758 days.

(21) Appl. No.: 11/246,722

(22) Filed: Oct. 6, 2005

(65) Prior Publication Data
US 2006/0121618 A1  Jun. 8, 2006

Related U.S. Application Data

(60) Provisional application No. 60/616,656, filed on Oct. 6, 2004.

(51) Int. Cl.
*G01N 33/48* (2006.01)
*G06F 19/00* (2011.01)
*C12N 15/87* (2006.01)

(52) U.S. Cl.
CPC ............... *G06F 19/00* (2013.01); *C12N 15/87* (2013.01)
USPC .......................................................... 702/19

(58) Field of Classification Search
None
See application file for complete search history.

(56) References Cited

U.S. PATENT DOCUMENTS

2004/0175838 A1 * 9/2004 Jarman et al. ................. 436/173

FOREIGN PATENT DOCUMENTS

WO  2004/008371 A1  1/2004

OTHER PUBLICATIONS

Altschul et al., Nucleic Acids Research, 1997, vol. 25, No. 17 3389-3402.*
Taylor et al., Anal. Chem., 2001, vol. 73, p. 2594-2604.*
Sunyaev et al. (Anal. Chem. 2003, 75, 1307-1315).*
Mann M., et al., "Error-Tolerant Identification of Peptides in Sequence Databases by Peptide Sequence Tags", Analytical Chemistry, American Chemical Society, vol. 66, No. 24, 1994, pp. 4390-4399.
Tabb, D.L., et al., "Gutentag: High-throughput Sequence Tagging Via an Empirically Derived Fragmentation Model" Analytical Chemistry, American Chemical Society, vol. 75, No. 23, 2003, pp. 6415-6421.
Tang, Wilfred H., et al., "Discovering Known and Unanticipated Protein Modifications Using MS/MS Database Searching", Analytical Chemistry, vol. 77, No. 13, 2005, pp. 3931-394.
International Search Report mailed Jul. 5, 2006 from International Appln. No. PCT/US2005/036027.

* cited by examiner

*Primary Examiner* — Pablo S Whaley
(74) *Attorney, Agent, or Firm* — John R. Kasha; Kelly L. Kasha; Kasha Law LLC

(57) ABSTRACT

The present teachings provide for identification of peptides using small sequence tags to focus computational resources on searching regions of a protein database that are the most likely to yield correct identifications. They allow for the incorporation of modifications and in doing so focuses the search to peptides with a precursor mass match. Additionally, probability or relevance factors can be used to determine peptide hypotheses. Various embodiments are presented that search for peptides when a single precursor is selected or when multiple precursors are simultaneously fragmented.

20 Claims, 5 Drawing Sheets

FASTA

408 — Protein 1
402 { MVSVTLG GSTNRGM PPLYGTM ACDEELF RKVMPQK CRTKVND VSADLLQ LKNDLET
      RVLYNKG STRGPKN LCVNSAA LKPIYWE QNWERTY VL
                                                    410  412  416
                                                              414

404 { Protein 2
      MSRKETG HIITRPY KFVMTKG QTL ........

Protein N

SCORED RANKED TAGS

| Tag | Score |
|---|---|
| 95 | ADL |
| 94 | VN |
| 87 | VS |
| 11 | LL |

406

RANKED PROTEIN SUBSEQUENCES (ALL) FROM FASTA

| Rank | Subsequence | Matching Tags | Score | Activity |
|---|---|---|---|---|
| 1 | VSADLLQ | ADL, VS, LL | 222 | high |
| 1e5 | LCVNSAA | VN | 158.3 | medium |
| 5e5 | HIITRPY | LL | 11 | low |
| 6e6 | LKPIYWE | none | 0 | none |

| Rank | Protein Segment | Tryptic | Semi-tryptic | Non-tryptic |
|---|---|---|---|---|
| 1 | VSADLLQ | X | | |
| 2 | ADLVNLL | X | X | X |
| 20000 | ACLGGNA | X | X | X |
| 100000 | LCVNSAA | X | X | X |
| 100001 | FGYCCTL | X | X | |
| 500000 | HIITRPY | X | | |
| 500001 | LKPIYWE | | | |

METHOD, SYSTEM, AND COMPUTER PROGRAM PRODUCT FOR SCORING THEORETICAL PEPTIDES

CROSS-REFERENCE TO RELATED APPLICATIONS

This application claims the benefit under 35 USC 119(e) of U.S. Provisional Application No. 60/616,656 filed on Oct. 6, 2004, which is incorporated herein by reference.

FIELD

The present teachings relate to the field of protein and peptide identification via mass spectrometry.

BACKGROUND

Identification of peptides and proteins is commonly performed by mass spectrometry. Typically, an unknown protein is digested using a site specific enzyme such as trypsin. The resulting peptides are ionized and passed into a first analyzer of a mass spectrometer. After selecting a precursor ion, the ion is fragmented and the intensities and the mass-to-charge ratios of the resulting fragment ions are measured by another mass analyzer. Peptide identification often proceeds by in silico digesting a database of potential protein sequence matches using the cutting rules of the enzyme used for the experimental digestion. Then, the theoretical peptides, also referred to as peptide hypotheses, or simply hypotheses, with a mass-to-charge ratio matching that of the precursor ion are theoretically fragmented to produce spectra. These theoretical spectra can be matched to the experimental spectrum, with the closest match indicating the most likely peptide. By performing this routine for several peptides, a likely candidate for the protein can be identified.

However, problems can exist when differences from a recognized protein state exist. These can be caused by a variety of circumstances including post-translational modification, the presence of single nucleotide polymorphisms, or other factors. These modifications can cause a difference in the precursor mass and/or the fragmentation of a peptide so that it does not correspond to the corresponding unmodified in silico peptide. This situation can preclude the proper peptide hypothesis from consideration and can result in situations such as a false weak match for the peptide, or no match at all. This in turn can decrease the confidence in subsequent protein identification. The present teachings can provide a method to identify protein and peptide sequences despite variations to the polypeptide's simplest form.

DESCRIPTION OF DRAWINGS

The skilled artisan will understand that the drawings, described below, are for illustration purposes only. The drawings are not intended to limit the scope of the present teachings in any way.

FIG. 4 represents data at various stages of processing by an embodiment of the present teachings.

DESCRIPTION

The section headings used herein are for organizational purposes only and are not to be construed as limiting the subject matter described in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Computer System Implementation

Figure 1:
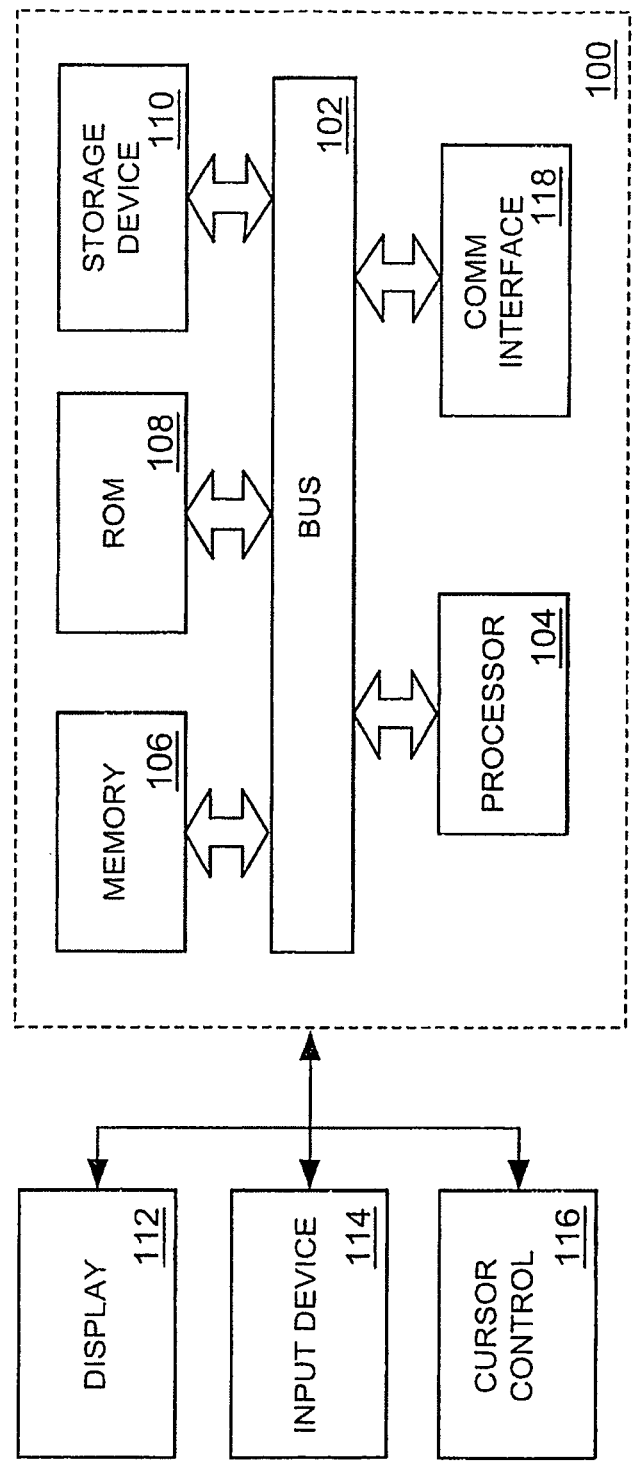
FIG. 1 illustrates an embodiment of a computer system upon which various embodiments of the present teachings can be implemented.

FIG. 1 is a block diagram that illustrates a computer system 100, according to certain embodiments, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102, and instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

Consistent with certain embodiments of the present teachings functions including spectrum input, database input, data storage, de novo tag calling, region of activity identification, candidate peptide determination, hypothesis generation peptide scoring, output and other aspects of the present teachings can be performed and results displayed by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of or in combination with software instructions to implement the invention. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

The foregoing description has been presented for purposes of illustration and description. It is not exhaustive and does not limit the invention to the precise form disclosed. Modifications and variations are possible in light of the above teachings or may be acquired from practice. Additionally, the described implementation includes software but the present teachings may be implemented as a combination of hardware and software or in hardware alone. The present teachings may be implemented with both object-oriented and non-object-oriented programming systems.

Figure 2:
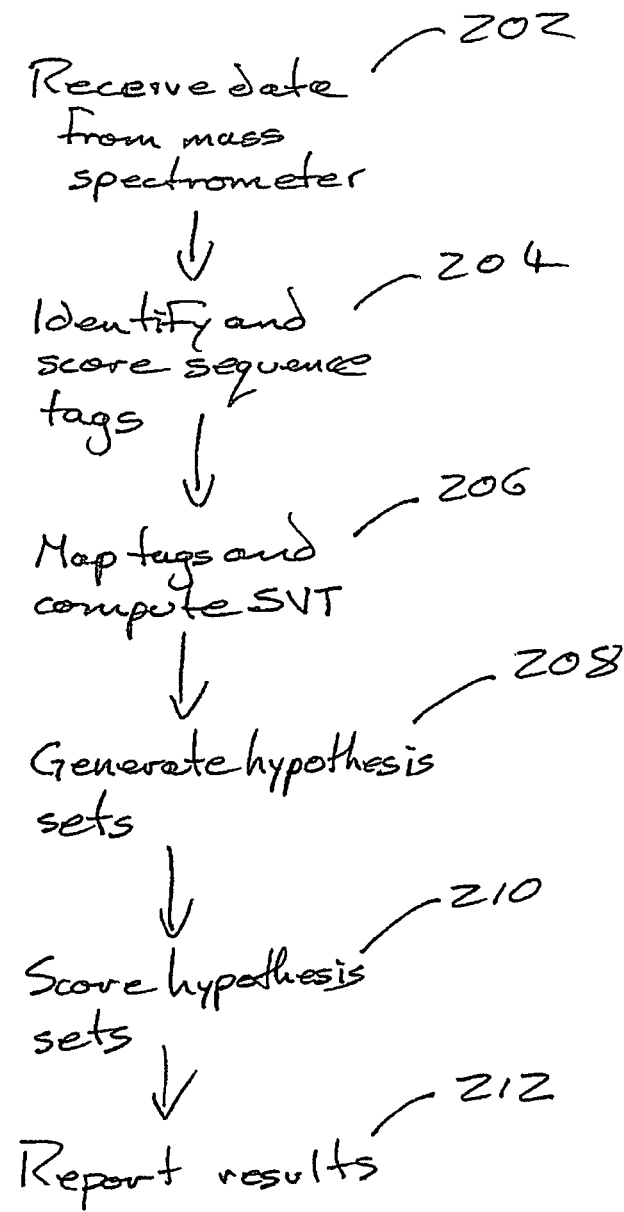
FIG. 2 illustrates an embodiment of the present teachings that can be used for peptide identification.

FIG. 2 illustrates an embodiment of the present teachings that can be used in peptide and protein identification. At 202, data is received from a mass spectrometry instrument. Such data can be in the form of data pairs, where one value represents a mass over charge value and the other variable represents intensity. In some cases, data quality values are also associated with the data pairs. This data can be stored in a computer memory for subsequent processing and future comparison. At 204, sequence tags are identified and scored from the mass spectrum data. Sequence tags can be generated by de novo sequencing techniques such as those presented in the literature (Taylor, J. A. and Johnson, R. S. *Rapid Commun. Mass Spectrom.* 1997, 11, 1067-1075, Dancik, V. et al, *J. Comput. Biol.* 1999, 6, 327-342.) While in some cases the entire sequence can be sequenced, in many cases, and in particular in the case of modifications, it may be possible to only sequence portions of the peptide. Thus only "tags" or short sections of the peptide may be properly identified. In addition to other methods that will be known to those skilled in the art, the present teachings contemplate a graph theoretic approach for finding sequence tags. Sequence tags can be almost any length. Some embodiments contemplate sequence tags that are two to three residues long although longer tags can be used. Also, longer sequences can be divided into smaller tags.

At 206, the sequence tags are mapped to various protein and peptide sequences contained in a database. A database can take many forms. For example it can be a relational database, or it can simply be a list of proteins contained on computer media or in computer memory. The database can be one of the many public databases such as UniProt, or it can be a proprietary database. Some embodiments, contemplate the use of a compressed database which can be used to consolidate redundancy. Such a database can contain information such as potential single nucleotide polymorphisms and splice variants. One skilled in the art will appreciate that the database can be constructed from information that is related to amino acids such as converting nucleotide sequence information into amino acid information. In some cases where the peptide, or a variant of it, is located in the database, either in isolation or as part of a longer amino acid sequence including full proteins, sequence tags will cluster. Scores can be computed over a portion of the sequence or over the entire sequence. These scores can be thought of as relating how "hot" a region of a sequence is. Consequently, these scores can be referred to as Sequence Temperature Values ("STV"). An STV can be determined on a continuous scale for all regions of sequence for all database entries, where a region can vary in size from a single amino acid to sequence segments of arbitrary length to whole proteins to genes or chromosome locations. One skilled in the art will recognize that there are many alternative methods to accomplish this ranking of regions, which may include other algorithmic or heuristic approaches.

At 208 a set of hypotheses is generated for each region. Hypothesis sets can be formed by looking in regions containing tag matches for hypotheses whose theoretical molecular weights as determined by the database sequence match the experimental precursor molecular weight. This can include hypothesis generation to account for modifications. The members of these sets can be determined in such a way that regions with high STVs have a hypotheses set with more and possibly less probable hypotheses whereas regions with low STVs are searched by a smaller set that may consist primarily of more probable hypotheses. In this way the computational resources required for scoring can be assigned to regions where a hypothesis match will more likely be found.

At 210, hypotheses are scored. One skilled in the art will appreciate that a variety of scoring methods exist. For example, theoretical fragmentation of the hypotheses can be performed and then matched to the mass spectrometer data from 202. Hypotheses that more closely match the experimental data as determined by the number of matching peaks receive a higher score than hypotheses will fewer matching peaks. One skilled in the art will appreciate that other scoring techniques can be used. At 212, the results are reported.

Identification of Sequence Tags

Some embodiments contemplate the use of graph theory to determine sequence tags. A variety of graph constructions can be formulated. Some embodiments build a directed graph where each vertex of the graph represents a fragment ion mass corresponding to a de-isotoped peak from the MS/MS spectrum and each edge of the graph represents an amino acid residue or a combination of two or more amino acid residues. An edge can be created between a pair of vertices if the difference in mass between the two vertices equals the amino acid mass(es) to within some user-specified tolerance. In some cases, the convention is adopted to direct edges from the lower-mass vertex to the higher-mass vertex. In some cases, there can be multiple edges leading into or out of a vertex.

Sequence tags can be identified by traversing the graph such that each potential path represents a hypothetical amino acid sequence. Paths can be scored by a variety of formulations. Some embodiments contemplate a scoring formulation whereby the path score is equal to the path peak intensities score multiplied by the fragment ions delta mass score multiplied by the gap penalty.

The path peak intensities score can be calculated by combining evidence based on peak intensity from all of the peaks in the path. For example, a larger peak intensity can imply strong evidence for that peak and thus can lead to a higher path peak intensities score. Some embodiments contemplate the use of corroborating peaks. For example, the presence of an additional peak at a mass 17 Daltons lower than the original peak can increase the evidence for the original peak as such a downstream peak can be indicative of a loss $NH_3$. As well, the presence of an additional peak at a mass 18 Daltons lower than the original peak can also increase the evidence for the original peak as such a downstream peak can be indicative of the loss of $H_2O$. The fragment ions delta mass score can measure how closely the experimental fragment ion masses match the theoretical masses obtained by in silico fragmentation of the hypothetical amino acid sequence under consideration.

The gap penalty can reduce the overall path score if gaps appear in the fragmentation ladder. This can indicate that the experimental MS/MS spectrum is missing one or more groups of one or more sequential peaks that would be expected from a hypothetical unmodified amino acid sequence undergoing complete fragmentation. Such gaps can be represented by edges in the graph.

Some embodiments generate path scores using the following equation, $$score = \left\{ 1 - \prod_{\text{all vertices } i \text{ in the path}} [1 - (b/y \text{ evidence for vertex } i)] \right\}$$

$$\int_{\mu-T/10}^{\mu+T/10} dm \frac{1}{\sqrt{2\pi\sigma^2}} e^{\frac{m^2}{2\sigma^2}}$$

where: µ represents the average of the delta masses in the path, σ represents the standard deviation of the delta masses in the path, and T represents a user-specified MS/MS tolerance One skilled in the art will appreciate that a plurality of scoring mechanisms can be employed. Some embodiments implement heuristics to limit scoring calculations to paths likely to yield a large score. For example during graph traversal, entire sections can be eliminated if the initial part of the path yields an unpromising score.

Given a selected path, sequence tags can be extracted. Some embodiments define a sequence tag as every two- or three-letter subsequence that contains no gaps. For example, if the selected path represents IVSNAS and there are no gaps, the sequence tags extracted are IV, VS, SN, NA, AS, IVS, VSN, SNA, and NAS. To facilitate further processing, each sequence tag is assigned a tag score. Some embodiments simply set the tag score equal to the path score. If there are multiple scores for any given sequence tag, thus indicating that it appears in multiple paths, some embodiments set the tag score to the highest scoring path.

Figure 3:
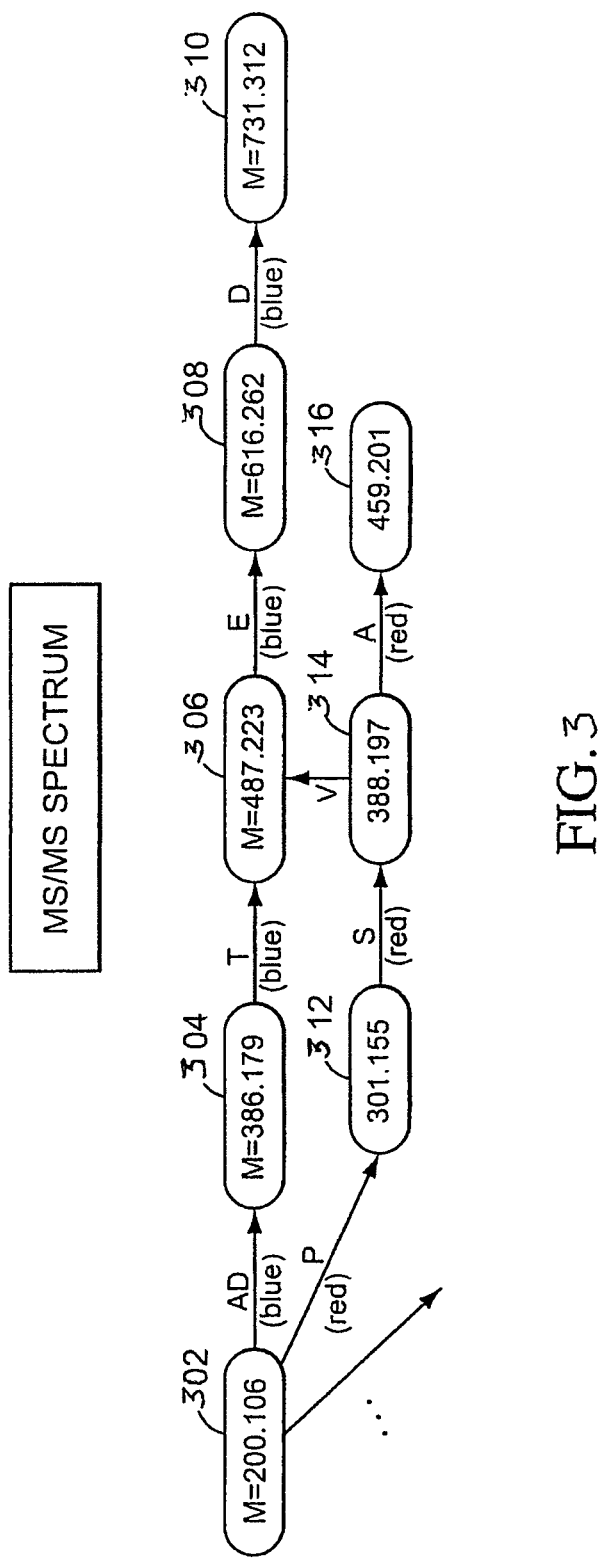
FIG. 3 illustrates an embodiment of the present teachings whereby a portion of an MS/MS spectrum is represented by a directed graph and paths representing putative peptide sequences are determined.

FIG. 3 illustrates an embodiment of the present teachings that constructs a graph from a mass spectra peak list. The mass spectrum peak list comprises eight peaks with mass to charge ratios of 200.106, 301.155, 386.179, 388.197, 459.201, 487.223, 616.262, and 731.312. A graph can be constructed by differencing the peaks and determining which differences are likely due to amino acids, or amino acid combinations. This can be accomplished by defining a threshold for which a difference is deemed to be close enough to the amino acid (or combination of amino acids) mass. For example, the transition between figure elements 306 and 308 is likely due to a Glutamic Acid (E) residue whose average monoisotopic mass is 129.115. This corresponds well to the value 616.262-487.223 which equals 129.039. Similarly, the transition between 302 and 304 whose mass difference is 186.073, is likely due to the combination of Alanine (A) and Aspartic Acid (D) whose average monoisotopic masses are 71.0788 and 115.0886 respectively. Another path could insert a Tryptophan (W) since its mass is approximately the same as the Alanine and Aspartic Acid combination. Different paths can be traced through the resulting graph. For example, one path can be represented by the sequence ADTED. If this sequence is determined to have a score of 0.9, then the sequence could give rise to tags, TED, TE, ED, each having a score of 0.9. Similarly, paths PSVED and PSA exist and could result in tags PSV, PS, SV, SVE, VE, VED, ED and PSA, PS, SA respectively. Some embodiments can relax the requirement that edges representing gaps by excluded from consideration when defining the tags. In the above example, this would allow the sequence AD to be considered as part of the sequence from which tags are extracted. Various embodiments also create vertices with complimentary masses where a complimentary mass is defined as the precursor mass minus the neutral mass derived from the fragment ion peak. In some instances, the number of such created vertices can be limited to some portion of the spectrum, for example the upper half or one third. Also, in various embodiments, a priori information about potential modifications can be taken into account by adding them to the list of amino acid masses.

In some cases, an initial vertex of mass zero can be included to mark the beginning of a b-ion fragment series. Similarly, an initial vertex of mass eighteen can be used to indicate the beginning of a y-ion series. In such cases, the direction of the resulting path can be reversed to indicate direction. As well, path finding need not necessarily start from a terminus; it can be formed using MS/MS fragmentation ladders arising from a series of internal ions.

Identification and Analysis of Regions

After scoring paths, extracting tags and scoring them, all tags or alternately a user-defined number of high scoring tags can be mapped to the sequence. A score can be generated for regions containing one or more tags. Scores can be computed over a portion of the sequence or over the entire sequence. These scores can be thought of as relating how "hot" a region of a sequence is. Consequently, these scores can be referred to as Sequence Temperature Values ("STV"). Various embodiments compute these scores by breaking the polypeptides sequences into amino acids subsequences called segments. The segments can vary or can be all of one length. If of fixed length, different values can be used. For example all segments might be 4 amino acids long, or they may be 10 amino acids long, or they may all be some length between or outside these values. Then, the tags can be matched against all of the segments and a score for each segment can be calculated. One method of scoring is to sum all of the scores of matching tags and also weighted scores of adjacent segments. For example, a weighting of one quarter or one third or some other suitable value can be used. Subsequences with the highest scores can be designated as regions of high STV and may be more likely to have a nearby peptide that correctly matches the experimental MS/MS spectrum.

FIG. 4 illustrates the process used by one embodiment of the present teachings. It shows two proteins (402, 404) from a FASTA file broken into seven amino acid segments. At 406 is shown a list of extracted sequence tags and their associated scores to be looked for in the segments. Segment one of Protein 1 contains one tag from the list, VS (408.) Segment six contains one tag from the list, VN (410.) Segment seven contains three tags from the list. These are: VS at 412, ADL at 414, and LL at 416. Consequently, each segment can be scored. For example, a segment can have a score comprising the scores of the sequence tags it contains (95, 87, and 11) and depending on the method chosen, a component related to the weighted scores of adjacent protein segments. If a weighting of one third is chosen, segment seven will have a score of 95+87+11+87/3 which equals 222. The scores are reflected in the sorted table at 420. Here, the segment VSADLLQ has the top score and can be designated as a region of high STV. Similarly, the segment CRTKVDN has high STV with a score of approximately 158.3. Other segments illustrated have much lower activity as indicated by their scores. The designation of activity STV levels and their score thresholds can be based on a variety measures. For example, they can be based on the number of protein segments that the user would like to retain for further analysis or they can be based on absolute score cutoffs or on some other metric.

Hypotheses can be generated by examining the regions containing tags. In some embodiments a cutoff for the number of highly scoring regions to be examined, for example 150, 500, 1000, or 2000 can be used. Many different criteria can be used to set the cutoffs. Regions can be examined by looking for candidate peptides containing the region itself as well as peptides in the region's vicinity. Modifications can be accounted for by hypothesizing their addition to the hypothesis when searching for precursor molecular weight matches. Some embodiments use the degree of activity of the region in order to determine the number of hypotheses to generate. For example, if a region is highly active, its neighborhood can be searched with more hypotheses than if it had low activity. In such cases, neighborhoods can be searched with more potential events. These events include modifications, substitutions, insertions, deletions, editing, trans-peptidation, crosslinking, etc. Each event generally has an associated probability which is related to the event's likelihood of occurrence. Events can also include semi-tryptic or non-tryptic digestions. Various embodiments rank the hypotheses based on the probabilities associated with their events. This ranking can be used when forming the hypothesis sets to be scored. For example the members of these sets can be determined in such a way that regions with high STVs have a hypotheses set with more and possibly less probable hypotheses whereas regions with low STVs are searched by a smaller set that may consist primarily of more probable hypotheses.

Figures 5A, 5B:
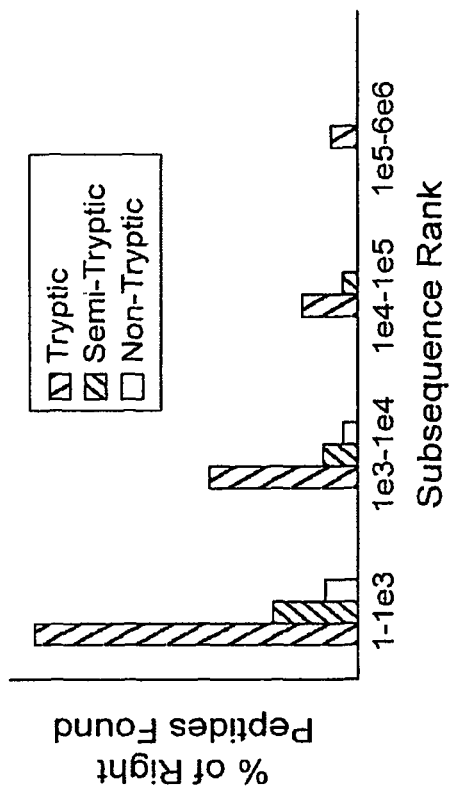
FIG. 5 demonstrates how an embodiment of the present teachings can limit the hypothesis search space by considering only certain types of digestion based upon a polypeptide region's score.

FIG. 5 illustrates the principle upon which some embodiments are based. FIG. 5a shows that in many cases, most of the correct answers regarding a peptide's sequence are found in the tryptic digest search space and that as the STV of a protein segment decreases, and consequently, its rank number increases, fewer correct answers are found in semi-tryptic digest, and still fewer correct answers are found in non-tryptic digest. One skilled in the art will appreciate that different hypothesis search spaces can be plotted in this fashion in order to determine which types of hypotheses should be attempted according to the degree of activity in the segment. This can have the effect of allocating search time so that highly active segments are more exhaustively examined than segments with low activity. FIG. 5b illustrates how an embodiment of the present teachings utilizes this information. It allows hypotheses formed from tryptic digests for the highest ranking five hundred thousand regions but only permits hypothesis formed by semi-tryptic digests the top ranking one hundred thousand regions and only permits non-tryptic digest based hypothesis for the top twenty thousand ranked segments. Hypotheses that return a peptide with a mass matching the experimental precursor masses can be identified as candidate peptides. Various embodiments take into account the close of match in between the hypothesis and precursor mass. For example, using knowledge of the expected variance in the data for the instrument producing the data, mass matches within 3 standard deviations of the theoretical of the peptide may be allowed for regions with high STV but matches for regions with low STV may require matches to be within one sigma. Knowledge of the expected or observed variance for the relevant instrument can be factored into these computations.

Hypotheses can be further examined by scoring via other methods. One skilled in the art will appreciate that a variety of methods exist. For example, the hypotheses can be theoretically fragmented into expected b and y ions, in order to generate a theoretical mass spectrum. This mass spectrum can then be scored against the experimental spectrum with each match between a theoretical ion and an experimental spectrum peak incrementing a spectrum-to-peptide match score by some value. In some embodiments, this value can be proportional to the spectral peak intensity, with larger values of the peak intensity corresponding to larger weights. The peptide(s) with the highest spectrum-to-peptide match scores can be reported to the user. One skilled in the art will appreciate that many different scoring methods can be found in the literature (Sadygov, R. G., Cociorva, D., and Yates, J. R. (2004) Nature Methods, Vol 1, No. 3, p195-202.)

The computational expense of protein database searching is generally proportional to the size of the database and the number of peptide variations (e.g. modifications and non-specific cleavages) allowed for in the search. The net combination of these and other factors determines the total search space the total number of hypotheses that are considered. Some embodiments address these factors by allowing only one of them to be large at any one time. In such approaches, a first search can be performed on a large database, but with minimal peptide variations. This can result in an overall search space that is small enough to remain tractable despite the size of the database The results of the first search can then be used to select a small number of database sequences, and a second search can be performed allowing for many peptide variations within this smaller database. In these teachings segments ranked below the cutoff can still be included if they result from very probable sequences. For example, segments from very probable protein sequences could be included at several times the cut-off depth while segments from less probable sequences might be allowed to pass only if they exceed the cutoff to a much smaller degree. Various embodiments set a cutoff in a total net effect of STV, protein probability, and peptide probability directly.

Various embodiments of the present teachings can allow for a soft-decision approach to addressing the size/variation search trade off. In such cases, rather than filtering out sequences, they can first be scored where the score can be based on correspondence to peptide sequences found in a previous search, or any a priori biological knowledge about the sample and the sequence. When ranking the segments, the database sequence score can be based on the aforementioned score (based on a priori information) in addition to the tag-matching score. This can result in database sequences with negligible evidence from biological context or previous searches still being identified due to tag-matching. In some instances, both sequence rank and segment rank can be taken into account to allow a variation space around more probable sequences and less around less likely sequences. This can yield a gain in speed by performing less scoring of precursor match hypotheses.

Some instances of the present teachings perform selective tag matching to realize a gain in speed by performing more limited scoring and tag matching by using knowledge of protein probabilities. For example, it may take higher quality fragmentation to meaningfully identify a peptide from an improbable protein. Thus the mass spectrometer data can include a spectral quality metric. Such a metric can be used in conjunction with proteins ranked based on their probability of occurring so that high-quality fragmentation may result in searching more less-probable proteins.

The present teachings can be applied to experiments where MS data is acquired at low-energy fragmentation to assess all potential precursors and all precursors are fragmented at the same time, without the normal selection of a single precursor, via high-energy fragmentation. In these cases, various types of correlation analysis can be performed. For example, in the case of mass spectrometry methods utilizing a separation technique prior to the mass spec instrument, correlation with time or covariation with fragmentation energy can be used to establish association of fragments with precursors. This can then allow identification of precursors via various embodiments that look for the conformance with a list of observed precursors instead of looking for the conformance of the theoretical mass for a particular peptide hypothesis with the observed single precursor. One skilled in the art will appreciate that there are numerous additional methods beyond this extension that permit the present teachings to work with low-high fragmentation data. For example, instead of analyzing the covariation of fragment peaks, covariation of tags and precursors with time can be established and then the association of tags with precursors, rather than fragment ions with precursors, can be established. This association need not be binary; a given tag can be associated with one precursor with a strong level of certainty while only weakly associated with another. Because a tag could have differing certainty for different precursor matches, the contribution a tag makes to the cumulative tag probabilities for segments producing matches to different precursors will likely be different. As well, the assessment of time dimension profiles can also be used to influence tag calling and tag probabilities. For example, a fragment ion that has a different time profile than all other peaks in a called tag may indicate some increased uncertainty in the local area of the tag, the whole tag, and any segment pointed to by this tag. Although low-high fragmentation generally produces very rich spectra, it is likely that a given fragment ion will be a part of more than one tag, and thus peaks that are cited in fewer tags can be viewed as having more discriminatory potential. Thus, tag probabilities and association with precursors can be adjusted to take this into account.

One skilled in the art will appreciate spectra collection can take several forms. For example a first mass analyzer can be used to select a molecular species. Alternately, no selection may be made at all and the resulting spectra contain peaks from multiple species. The present teachings can be used in either case.

The Use of Feature Probabilities

Various embodiments provide for considering the joint effect of various features such as modifications, mutations, etc., to create new types of events that can affect hypothesis generation. This can also have the effect of limiting the number of decisions that result in complete filtering out of polypeptides from the identification/search process. For example some search methodologies require the user to specify 1) the types of modifications expected and/or 2) the set of digestion features permitted and/or 3) what species are to be considered. Such rules are binary in nature so that all features outside any set bounds are lost and, often, all features inside the bounds are valued equally, regardless of their degree of conformance to expectation. As well, numerical settings such as mass tolerances can cause similar binary decisions. Additional features that other identification methodologies may require binary decisions for include charge states, allowed amino acid substitutions, and fragment ion types. Various embodiments allow each of these types of features or settings to be treated with probabilities, or other ranking method, that indicates the relative importance of that feature. Thus while forming hypotheses, these probabilities can be used dynamically. For example, the net effect of multiple factors can be considered. This can differentiate between a situation where a certain feature is highly probable when in the presence of certain features but has a very low probability of being present when in the presence of other features.

Various embodiment assign values to the features that reflect their relative importance and/or chance of occurring. These can be probabilistic in nature or can be rooted in other methodologies such as heuristic rules. While forming hypotheses, these values/rules can be used dynamically. For example, the net effect of multiple values/rules can be considered. (For sake of convenience, the following discussion will deal primarily with describing these values/rules as probability values but one skilled in the art will appreciate that other values or rules can be substituted into the present teachings.) This can be used to differentiate between a situation where a certain feature is highly probable when in the presence of certain features but has a very low probability of being present when in the presence of other features.

Modifications are one feature type that can be used in accordance with these teachings. For example, there are a number of different types of modifications that can appear as part of a protein or peptide hypothesis. Some of these are the result of natural biological processes such as phosphorylation, and some are the result of the preparation of the sample in the laboratory by the scientist. A modification feature could be assigned a probability of occurrence at a particular amino acid by finding all instances where the modification does occur divided by the total number of instances of the residue. The specificity of a modification with its associated probability could be described in terms of single amino acids or more complex patterns such as consensus sequences.

Digestion features are another type of feature that can be used in forming hypotheses. Samples of proteins are frequently treated with proteolytic agents such as proteases in order to break the proteins into peptides with expected cleavage features. Digest features can also be treated with probabilities. A probability for a given digest method such a trypsin digestion resulting in a cleavage at a particular site—for example the expected cleavage between Lysine and Proline—can be determined by observing what portion of occurrences of this bond are actually observed to be cleaved in real results from tryptic digestions. The frequency of cleavages at any and all sites can be learned from real data. Analogous to modifications, the specificity of a potential cleavage site can be described as a pair of amino acids or more complex sequence patterns. The probability of missed cleavages can be implied from knowledge of cleavage probabilities. Although the cleavages are not the result of an actual digestion treatment, an effective set of digest probabilities can be learned for samples analyzed with post-source decay whereby large polypeptides are effectively cleaved in the mass spectrometer and then fragmented. Samples of naturally digested peptides isolated from biological samples—so called 'peptidome' samples—can also yield useful digest frequency patterns.

The difference between the observed precursor mass and the theoretical mass of the peptide hypothesis (delta mass) can also be treated as a feature and modeled with probabilities. Various embodiments assign probability to a particular difference between an observed and a theoretical mass or m/z of a peptide using knowledge of the expected variance for a given instrument type and some knowledge of how well the instrument is calibrated (precision and accuracy.

Probability can also be assigned to substitution features using both empirical information as with modifications and/or evolutionary distance matrices.

Other features that can be modeled with probabilities and used in the manner described include, any measure of the quality of tag evidence that can be derived from the spectrum, or any other properties consistent with the principles illustrated with the provided list of examples, probabilities of amino acid or nucleic acid substitutions, insertions, deletions, or combinations of these probabilities of sequence processing events such as terminal processing or editing, the probability of the observed mass defect, attributes of a database of known proteins, transcripts, or genes such as the size in number of sequences or megabytes, any attribute of the quality of fragmentation evidence, including the likelihood that a single peptide is being observed in isolation based on the spectral evidence at the MSN-1 level, the signal to noise properties for fragmentation peaks, characteristic ions evidence (e.g. expected neutral losses from particular modifications), etc.

One skilled in the art will appreciate that other mathematical or heuristic constructs can be employed to effect the concept of ranking or rating the importance features and preventing binary decisions about which features/settings to use in a search. Similarly, the assessment of the net effect of multiple factors is discussed in terms of combinations of these probabilities as a joint probability, however other mathematical or heuristic constructs can accomplish the same objective.

Species Probability

Conformance of the species of origin for a particular hypothesis relative to the species known to be present in the sample can also be treated as a type of feature of a hypothesis and treated with probabilities. Various embodiments employ a species-species matrix describing the ultility of searching outside the expected species (extraspecies) for one or more additional species. Several factors that can influence the chance of a correct peptide sequence answer being found in the sequence of a protein from a species other than the expected one, include, the evolutionary distance to the expected species (homology), the complexity of the organism (size of its proteome), and the degree to which the organism has been studied and thus represented in protein databases (completeness of the proteome).

Any or all of these factors can be used to create a matrix that describes the utility of searching outside the expected species. The matrix rows can be derived empirically. With a large amount of data, the frequency with which all other species yield correct answers can be determined with samples from any given species.

Some implementations of the present teachings assess a net effect or net probability for the overall peptide hypothesis. This can be used to reject a hypothesis containing two marginally probable features, for example an unusual modification in combination with one terminus that has a lower probability digest pattern.

Some implementations of the present teachings may recognize that the features are largely independent of each other and assess the net probability of a peptide hypothesis by computing the joint probability among the plurality of features associated with the hypothesis. For example, if the chance of oxidation occurring on methionine is 0.1 and the chance of a mouse protein sequence being the best answer when searching a human sample is 0.1, the cumulative chance of correct peptide from a mouse sequence with an oxidized methionine is $0.1*0.1=0.01$. If it is assumed (incorrectly) that there are only two states of methionine—with and without oxidation—the probability of unmodified methionine would then be 0.9 If species probability is treated by normalizing to the maximal value for the relevant row of a species-species probability matrix, the probability of a human protein sequence being the best match to a spectrum from a human sample would be 1.0. Thus, the cumulative chance of a peptide with unmodified methionine from a human sequence in the same sample would be $1.0*0.9=0.90$ which is far more likely than an oxidized methionine in a mouse sequence.

Various embodiments allow the user to control the balance between the quality of spectral evidence as quantified by the strength of tag implication in the STV and the improbability of the peptide hypothesis or the features of a hypothesis. For example, a sequence region with very high STV merits consideration of even highly unlikely peptide hypotheses, because there is substantial fragment evidence present to substantiate unlikely hypotheses. At the other limit, a sequence region with very low STV does not warrant the consideration of improbable hypotheses; only highly believable hypotheses should be considered or scored because there is not enough fragmentation evidence to substantiate anything less than highly likely peptide types. Various embodiments implement this by presenting the user with the choice of performing a "rapid", "thorough", or "exhaustive" search. These settings can then be translated into probability cutoffs. For example, in the rapid limit, a high cutoff can be established so the only very probable hypotheses for a given degree of STV will be considered, while in the other settings, the same level of STV would warrant consideration of much less probable peptides.

Some implementations of more conventional database search algorithms that do not employ probabilistic tags can also benefit from the use of feature probabilities, despite the lack of STVs. If the setting for this overall threshold is greater than the cumulative probability of a particular combination of features, that combination of features would be not considered. Thus without STVs, the exploration of search space is governed by the same inequality relationship between some overall cutoff and the combined consideration of SVT and peptide probability except that all regions have effectively the same temperature.

Emphasis Factors

Various embodiments employ an emphasis factor that modifies normal probability associated with a feature. For example, an artificially high value could be set to emphasize searching for a particular feature. This may be used to focus on a particular type of hypothesis, such as hypotheses involving methylation because the user is interested in this category of peptides. For example, the real probability of phosphorylation on serine might be 0.05 based on the normal rate observed in biological samples. The user may be interested in finding as many phosphorylations as possible and would employ an emphasis factor to increase the chance of finding such modifications. Internally the result of this direction from the user would be to substitute the emphasis factor times the real probability in place of the real expected biological rate of the modification. Alternately, the prior could simply be replaced with some pre-determined value like 1.0. The best choice between these options may depend on the situation.

Various embodiments maintain the distinction between emphasis factors and the real priors so that the real priors are used in calculating the actual confidence in the answers. In general, emphasis factors can be applied to almost any feature or joint set of features. For example, emphasis factors can be used to emphasize a biological process, molecular function, or pathway. For example, the user might always search for kinases or histones.

The invention claimed is:

1. A system for scoring theoretical peptides used to identify peptides in a sample, comprising:
   a database that stores a plurality of known peptide sequences;
   a mass spectrometer that analyzes the sample by selecting a precursor ion, fragmenting the precursor ion and producing fragment ion data; and
   a processor in communication with the mass spectrometer and the database that
   a) receives the fragment ion data from the mass spectrometer,
   b) identifies a plurality of sequence tags from the fragment ion data,
   c) compares the plurality of sequence tags to one or more sequence segments of each peptide sequence of the plurality of known peptide sequences in the database, and scores each segment of the one or more sequence segments based on tag scores of sequence tags from the plurality of sequence tags included by each segment producing a plurality of scored segments,
   d) generates a plurality of peptide features that affect theoretical peptide generation and associates a probability with each feature that indicates a sample implied frequency of each peptide feature, wherein the plurality of peptide features include one or more of modifications, digestions, species of origin, or mutations,
   e) generates, for each scored segment of the plurality of scored segments, one or more theoretical peptides by,
      (i) calculating a feature probability threshold based on the score of the segment so that the higher the score of segment the lower the feature probability threshold,
      (ii) generating one or more theoretical peptides for the segment by applying each peptide feature of the plurality of peptide features that has a probability above the feature probability threshold to the segment, and
      (iii) selecting each theoretical peptide of the one or more generated theoretical peptides that has a mass within a mass tolerance of the mass of the precursor ion, and
   f) scores the one or more theoretical peptides for each scored segment by performing a comparison of each theoretical peptide with the fragment ion data.

2. The system of claim 1, wherein the processor adjusts a score of a scored segment of the plurality of scored segments by adding to the score a component related to a weighted score of one or more segments adjacent to the scored segment.

3. The system of claim 1, wherein the processor reduces the size of the plurality of scored segments before the processor generates one or more theoretical peptides for each scored segment of the plurality of scored segments by setting a maximum number of scored segments to be examined, maintaining the maximum number of scored segments that have the highest scores in the plurality of scored segments, and removing a remainder of scored segments from the plurality of scored segments.

4. The system of claim 1, wherein the processor generates one or more theoretical peptides for each scored segment of the plurality of scored segments by considering post-translational modifications.

5. The system of claim 1, wherein the processor generates one or more theoretical peptides for each scored segment of the plurality of scored segments by considering digestion features.

6. The system of claim 1, wherein the processor generates one or more theoretical peptides for each scored segment of the plurality of scored segments by considering single nucleotide polymorphisms.

7. The system of claim 1, wherein the processor generates one or more theoretical peptides for each scored segment of the plurality of scored segments by considering phosphorylation.

8. The system of claim 1, wherein the processor assigns a probability to each theoretical peptide generated for a scored segment.

9. A method for scoring theoretical peptides used to identify peptides in a sample, comprising:
   a) analyzing the sample by selecting a precursor ion, fragmenting the precursor ion and producing fragment ion data using a mass spectrometer;
   b) receiving fragment ion data from the mass spectrometer using a processor;
   c) identifying a plurality of sequence tags from the fragment ion data using the processor;
   d) comparing the plurality of sequence tags to one or more sequence segments of each peptide sequence of a plurality of known peptide sequences stored in a database and scoring each segment of the one or more sequence segments based on tag scores of sequence tags from the plurality of sequence tags included by each segment producing a plurality of scored segments using the processor;
   e) generating a plurality of peptide features that affect theoretical peptide generation and associating a probability with each feature that indicates a sample implied frequency of each peptide feature, wherein the plurality of peptide features include one or more of modifications, digestions, species of origin, or mutations;
   f) generating, for each scored segment of the plurality of scored segments, one or more theoretical peptides by,
      (i) calculating a feature probability threshold based on the score of the segment so that the higher the score of segment the lower the feature probability threshold,
      (ii) generating one or more theoretical peptides for the segment by applying each peptide feature of the plurality of peptide features that has a probability above the feature probability threshold to the segment, and
      (iii) selecting each theoretical peptide of the one or more generated theoretical peptides that has a mass within a mass tolerance of the mass of the precursor ion; and
   g) scoring the one or more theoretical peptides for each scored segment by performing a comparison of each theoretical peptide with the fragment ion data using the processor.

10. The method of claim 9, further comprising adjusting a score of a scored segment of the plurality of scored segments by adding to the score a component related to a weighted score of one or more segments adjacent to the scored segment.

11. The method of claim 9, further comprising reducing the size of the plurality of scored segments before generating one or more theoretical peptides for each scored segment of the plurality of scored segments by setting a maximum number of scored segments to be examined, maintaining the maximum number of scored segments that have the highest scores in the plurality of scored segments, and removing a remainder of scored segments from the plurality of scored segments using the processor.

12. The method of claim 9, wherein generating one or more theoretical peptides for each scored segment of the plurality of scored segments using the processor comprises considering post-translational modifications.

13. The method of claim 9, wherein generating one or more theoretical peptides for each scored segment of the plurality of scored segments using the processor comprises considering digestion features.

14. The method of claim 9, wherein generating one or more theoretical peptides for each scored segment of the plurality of scored segments using the processor comprises considering single nucleotide polymorphisms.

15. The method of claim 9, wherein generating one or more theoretical peptides for each scored segment of the plurality of scored segments using the processor comprises considering phosphorylation.

16. The method of claim 9, further comprising assigning a probability to each theoretical peptide generated for a scored segment using the processor.

17. The method of claim 16, wherein the probability assigned to each theoretical peptide using the processor is associated with a probability of one or more sequence events that can affect the scored segment.

18. The method of claim 17, wherein the one or more sequence events comprise a modification, a substitution, an insertion, a deletion, an edit, trans-peptidation, or crosslinking.

19. The method of claim 9, further comprising generating one or more theoretical peptides for each scored segment of the plurality of scored segments using the processor so that a probability of a theoretical peptide of the number of theoretical peptides is indirectly proportional to the score of each scored segment.

20. A computer program product, comprising a computer-readable storage medium whose contents include a program with instructions being executed on a processor so as to perform a method for scoring theoretical peptides used to identify peptides in a sample, the method comprising:
   a) providing a system, wherein the system comprises distinct software modules, and wherein the distinct software modules comprise a receiving data module, an identifying sequence tags module, a mapping sequence tags module, a generating theoretical peptides module, and a scoring theoretical peptides module;
   b) receiving fragment ion data produced by a mass spectrometer that analyzed the sample by selecting a precursor ion and fragmenting the precursor ion using the receiving data module;
   c) identifying a plurality of sequence tags from the fragment ion data using the identifying sequence tags module;
   d) comparing the plurality of sequence tags to one or more sequence segments of each peptide sequence of a plurality of known peptide sequences stored in a database and scoring each segment of the one or more sequence segments based on tag scores of sequence tags from the plurality of sequence tags included by each segment producing a plurality of scored segments using the mapping sequence tags module;
   e) generating a plurality of peptide features that affect theoretical peptide generation and associating a probability with each feature that indicates a sample implied frequency of each peptide feature, wherein the plurality of peptide features include one or more of modifications, digestions, species of origin, or mutations;
   f) generating, for each scored segment of the plurality of scored segments, one or more theoretical peptides by,
      (i) calculating a feature probability threshold based on the score of the segment so that the higher the score of segment the lower the feature probability threshold,
      (ii) generating one or more theoretical peptides for the segment by applying each peptide feature of the plurality of peptide features that has a probability above the feature probability threshold to the segment, and
      (iii) selecting each theoretical peptide of the one or more generated theoretical peptides that has a mass within a mass tolerance of the mass of the precursor ion; and
   g) scoring the one or more theoretical peptides for each scored segment by performing a comparison of each theoretical peptide with the fragment ion data using the scoring theoretical peptides module.

* * * * *